United States Patent [19]
Alferness et al.

[11] Patent Number: 5,766,224
[45] Date of Patent: Jun. 16, 1998

[54] TEMPORARY, POST-HEART SURGERY CARDIOVERTING AND PACING SYSTEM AND LEAD SYSTEMS FOR USE THEREIN

[75] Inventors: Clifton A. Alferness, Redmond; John M. Adams, Issaquah; Gregory M. Ayers, Redmond; Hugo X. Gonzalez, Woodinville, all of Wash.

[73] Assignee: InControl, Inc., Redmond, Wash.

[21] Appl. No.: 627,688

[22] Filed: Apr. 2, 1996

[51] Int. Cl.⁶ ..................................... A61N 1/05
[52] U.S. Cl. ................. 607/4; 607/129; 607/132
[58] Field of Search ................. 607/4, 5, 10, 33, 607/123, 132, 130, 129

[56] References Cited

U.S. PATENT DOCUMENTS

| | | | |
|---|---|---|---|
| 3,333,045 | 7/1967 | Fisher et al. | 607/132 |
| 3,807,411 | 4/1974 | Harris et al. | 607/10 |
| 4,144,889 | 3/1979 | Tyers et al. | 607/130 |
| 4,541,440 | 9/1985 | Parsonnet | 607/132 |
| 5,403,351 | 4/1995 | Saksena | 607/5 |
| 5,403,353 | 4/1995 | Afemess et al. | 607/10 |

OTHER PUBLICATIONS

Parsonnet et al., "A technique for postoperative application of a newly designed temporary bipolar dual-chamber pacemaker electrode," Journal of Thoracic Cardiovascular Surgury, 89:456-458, 1985 (607/132).

*Primary Examiner*—Jeffrey R. Jastrzab
*Attorney, Agent, or Firm*—Richard O. Gray, Jr.

[57] ABSTRACT

A post-surgical atrial cardioverting, atrial pacing, and ventricular pacing system and lead system provides for cardioverting the atria, pacing the atria, and/or pacing the ventricles of the heart of a post-surgical heart patient. The system includes a first lead and a second lead providing a pair of atrial cardioverting electrodes, an atrial pacing electrode, and a ventricular pacing electrode. The electrodes are electrically isolated from each other. The system further includes at least one anchor releasably disposing the electrodes beneath the skin of the patient with each atrial cardioverting electrode electrically contacting a respective given one of the atria, the atrial pacing electrode electrically contacting one of the atria, and the ventricular pacing electrode electrically contacting a ventricle. The system further includes at least one of an external cardiovertor coupled to the cardioverting electrodes for cardioversion, an external atrial pacer coupled to the atrial pacing electrode and one of the atrial cardioverting electrodes for pacing the atria, and an external ventricular pacer coupled to the ventricular pacing electrode and one of the atrial cardioverting electrodes for pacing the ventricles.

13 Claims, 5 Drawing Sheets

5,766,224

TEMPORARY, POST-HEART SURGERY CARDIOVERTING AND PACING SYSTEM AND LEAD SYSTEMS FOR USE THEREIN

BACKGROUND OF THE INVENTION

The present invention is generally directed to a cardioverting system for providing temporary cardioversion and/or pacing of the heart of a heart surgery patient following a heart surgery procedure. The present invention is more particularly directed to lead systems for use in such cardioverting systems.

There are approximately four hundred thousand (400,000) heart surgery procedures performed annually in the United States. The types of such surgical procedures vary from coronary artery bypass grafts to valve replacements, to repair of congenital heart defects. In order to gain access to the heart, most of these surgeries require the chest to be opened in the middle of the sternum. An incision is then made in the pericardial sac (pericardium) to expose the heart and permit the required surgical procedure to be performed. Following the surgical procedure, the pericardial incision is reapproximated (closed except for a drain opening) with sutures and the chest cavity is closed.

Often, during recovery following such heart surgical procedures, the patients' hearts experience bradycardia (slow heart rates). In the prior art, to overcome such maladies, the hearts of post-surgical heart patients are temporarily paced for a few days following surgery, when required, to maintain the heart rates at a normal rate. This is accomplished by releasably attaching heart pacing wires to the heart before the pericardium is sutured and the chest cavity is closed. First and second heart pacing wires are attached to the myocardium of the heart, usually one of the ventricles such as the left ventricle. The heart pacing wires are then brought outside of the chest. Thereafter, the pericardium is sutured and the chest cavity is closed. The proximal ends of the heart pacing wires are then coupled to a temporary pacemaker to permit the heart to be paced. After the patient has recovered sufficiently wherein pacing is no longer required, the heart wires are pulled out of the patient.

In addition to bradycardia, twenty to thirty percent of all heart surgical patients experience an arrhythmia called atrial fibrillation during the immediate or early post-surgical period. When this occurs, the heart beats rapidly and irregularly. According to reports, this constitutes a major clinical problem resulting in hypotension, heart failure, pneumonia and/or stroke, due to thromboembolism. Hence, such a condition is of great concern to the physician and it is therefore in the best interest of the patient to terminate this arrhythmia as soon as possible.

The development of post-surgical atrial fibrillation has not been clearly associated with preoperative or postoperative clinical predictors. Further, the specificity and sensitivity of age and other possible relevant factors for prediction of atrial fibrillation after heart surgery is low. No effective prophylactic regimen has yet been established.

When atrial fibrillation of a surgical patient's heart occurs during surgery, the physician terminates the fibrillation by cardioverting the heart. In this cardioversion procedure, the physician contacts each atria with a spoon-sized conductive paddle which is coupled to an external defibrillator. The external defibrillator includes a storage capacitor which is charged to a selected voltage. When the storage capacitor is fully charged, the stored energy is discharged into the atria of the heart through the paddles.

While the above-mentioned cardioverting process is very effective in terminating atrial fibrillation occurring during surgery, this procedure is not available to the physician for terminating atrial fibrillation occurring after the heart surgery is completed and the patient's chest cavity has been closed. It has been observed that the peak incidence of atrial fibrillation is up to the seventh postoperative day. While external cardioversion is an option, because the patient's chest cavity at this time is closed, much larger paddles and much greater cardioverting energies must be used as compared to the paddle size and cardioverting energies employed during surgery. Such energies, generally between 50 and 360 joules, would also require the patient to be briefly anesthetized or sedated prior to attempted external cardioversion. Hence, while external cardioversion, using much larger paddles and much higher cardioverting energies, is available to the physician as an option, most physicians would prefer to avoid such external cardioversion because of the likely trauma and tissue damage it would cause the patient during a time in which the patient is in a critical in initial recovery phase from open heart surgery.

Drug therapy is also an available option. Its use however is often attended with in effectiveness, potential harm and significant side effects. In addition, there is a substantial potential interaction of such drugs with the many different types and amounts of other drugs the patient is already receiving during this initial recovery period.

U.S. Pat. No. 5,403,353 discloses one cardioverting system and method capable of arresting fibrillation, such as atrial fibrillation, occurring during the post-heart surgery period. The system and method there disclosed does not cause prolongation of the patient's recovery period due to trauma and tissue damage and avoids the need for drug therapy to treat such a condition. To accomplish this end, a pair of temporary leads are releasably anchored beneath the skin of the patient during the open chest surgical procedure. Each lead is provided with an elongated electrode which is disposed in electrical contact with one of the atria. The temporary leads are then available to apply comparatively low voltage cardioverting energy to the atria when the atria are in need of cardioversion. When the leads are no longer needed, they can be pulled from the patient's body.

The present invention is directed to such a system which combines the additional functions of atrial and ventricular sensing and pacing in the temporary cardioversion leads. This permits atrial cardioversion, atrial sensing and pacing, and ventricular sensing and pacing without the need for separate heartwires to achieve the sensing and pacing functionality.

SUMMARY OF THE INVENTION

The present invention provides a post-surgical temporary electrode system for applying atrial cardioverting electrical energy and/or pacing energy to the heart of a post-surgical heart patient. The system includes a first lead and a second lead providing a pair of atrial cardioverting electrodes, an atrial pacing electrode, and a ventricular pacing electrode. The electrodes are electrically isolated from each other. The lead system further includes at least one anchor releasably disposing the electrodes beneath the skin of the patient with each atrial cardioverting electrode electrically contacting a respective given one of the atria, the atrial pacing electrode electrically contacting one of the atria, and the ventricular pacing electrode electrically contacting a ventricle.

The invention further provides post-surgery temporary lead system for applying atrial cardioverting electrical energy and/or pacing energy to the heart of a post-surgical heart patient. The system includes a first lead having an atrial pacing electrode, an atrial cardioverting electrode, and a ventricular pacing electrode, wherein the electrodes are electrically isolated from each other and spaced apart so that when the atria pacing and cardioverting electrodes are in electrical contact with an atrium, the ventricular pacing electrode is in electrical contact with a ventricle and a second lead having an atrial cardioverting electrode. The lead system further includes at least one anchor releasably disposing the electrodes beneath the skin of the patient with the atrial pacing electrode of the first lead electrically contacting a given one of the atria, the atrial cardioverting electrode of the first lead electrically contacting the given one of the atria, the ventricular electrode of the first lead electrically contacting a given one of the ventricles and the atrial cardioverting electrode of the second lead electrically contacting the other one of the atria.

The invention still further provides a post-surgical temporary lead system for applying atrial cardioverting electrical energy and/or pacing energy to the heart of a post-surgical heart patient. The system includes a first lead having an atrial pacing electrode and an atrial cardioverting electrode, the electrodes being electrically isolated from each other and spaced apart so that when the cardioverting electrode of the first lead is in electrical contact with an atrium, the atrial pacing electrode of the first lead is in electrical contact with the atrium. The lead system further includes a second lead having an atrial cardioverting electrode and a ventricular pacing electrode. The electrodes of the second lead are electrically isolated from each other and spaced apart so that when the atrial cardioverting electrode of the second lead is in electrical contact with an atrium, the ventricular electrode of the second lead is in electrical contact with a ventricle. The lead system further includes at least one anchor releasbly disposing the electrodes beneath the skin of the patient with the atrial cardioverting electrode of the first lead electrically contacting a given one of the atria, the atrial pacing electrode of the first lead electrically contacting the given one of the atria, the atrial cardioverting electrode of the second lead electrically contacting the other one of the atria and the ventricular pacing electrode of the second lead electrically contacting a ventricle.

The present invention also provides a post-surgical atrial cardioverting, atrial pacing, and ventricular pacing system for cardioverting the atria, pacing the atria, and/or pacing the ventricles of the heart of a post-surgical heart patient. The system includes a first lead and a second lead providing a pair of atrial cardioverting electrodes, an atrial pacing electrode, and a ventricular pacing electrode. The electrodes are electrically isolated from each other. The system further includes at least one anchor releasably disposing the electrodes beneath the skin of the patient with each atrial cardioverting electrode electrically contacting a respective given one of the atria, the atrial pacing electrode electrically contacting one of the atria, and the ventricular pacing electrode electrically contacting a ventricle, and at least one of an external cardiovertor coupled to the cardioverting electrodes for cardioversion, an external atrial pacer coupled to the atrial pacing electrode and one of the atrial cardioverting electrodes for pacing the atria, and an external ventricular pacer coupled to the ventricular pacing electrode and one of the atrial cardioverting electrodes for pacing the ventricles.

The invention further provides a post-surgical atrial cardioverting, atrial pacing, and ventricular pacing system for cardioverting the atria, pacing the atria, and/or pacing the ventricles of the heart of a post-surgical heart patient. The system includes a first lead having an atrial pacing electrode, an atrial cardioverting electrode, and a ventricular pacing electrode, the electrodes being electrically isolated from each other and spaced apart so that when the atrial pacing and cardioverting electrodes are in electrical contact with an atrium, the ventricular pacing electrode is in electrical contact with a ventricle and a second lead having an atrial cardioverting electrode. The system further includes at least one anchor releasably disposing the electrodes beneath the skin of the patient with the atrial pacing electrode of the first lead electrically contacting a given one of the atria, the atrial cardioverting electrode of the first lead electrically contacting the given one of the atria, the ventricular electrode of the first lead electrically contacting a given one of the ventricles and the atrial cardioverting electrode of the second lead electrically contacting the other one of the atria, and at least one of an external cardiovertor coupled to the cardioverting electrodes for cardioversion, an external atrial pacer coupled to the atrial pacing electrode and one of the atrial cardioverting electrodes for pacing the atria, and an external ventricular pacer coupled to the ventricular pacing electrode and one of the atrial cardioverting electrodes for pacing the ventricles.

The invention still further provides a post-surgical atrial cardioverting, atrial pacing, and ventricular pacing system for cardioverting the atria, pacing the atria, and/or pacing the ventricles of the heart of a post-surgical heart patient. The system includes a first lead having an atrial pacing electrode and an atrial cardioverting electrode, the electrodes of the first lead being electrically isolated from each other and spaced apart so that when the cardioverting electrode of the first lead is in electrical contact with an atrium, the atrial pacing electrode of the first lead is in electrical contact with the atrium, and a second lead having an atrial cardioverting electrode and a ventricular pacing electrode, the electrodes of the second lead being electrically isolated from each other and spaced apart so that when the atrial cardioverting electrode of the second lead is in electrical contact with an atrium, the ventricular electrode of the second lead is in electrical contact with a ventricle. The system further includes at least one anchor releasably disposing the electrodes beneath the skin of the patient with the atrial cardioverting electrode of the first lead electrically contacting a given one of the atria, the atrial pacing electrode of the first lead electrically contacting the given one of the atria, the atrial cardioverting electrode of the second lead electrically contacting the other one of the atria and the ventricular pacing electrode of the second lead electrically contacting a ventricle, and at least one of an external cardiovertor coupled to the cardioverting electrodes for cardioversion, an external atrial pacer coupled to the atrial pacing electrode and one of the atrial cardioverting electrodes for pacing the atria, and an external ventricular pacer coupled to the ventricular pacing electrode and one of the atrial cardioverting electrodes for pacing the ventricles.

In accordance with one preferred embodiment, the first and second leads each have a longitudinal dimension and are joined together along the longitudinal dimensions beginning from a point proximal to the cardioverting electrodes and distal to and continuing proximally through and past a point of exit from the patient to provide a single lead body for extraction.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several figures of which like reference numerals identify identical elements, and wherein:

DETAILED DESCRIPTION OF THE PREFERRED EMBODIMENT

Figure 1:
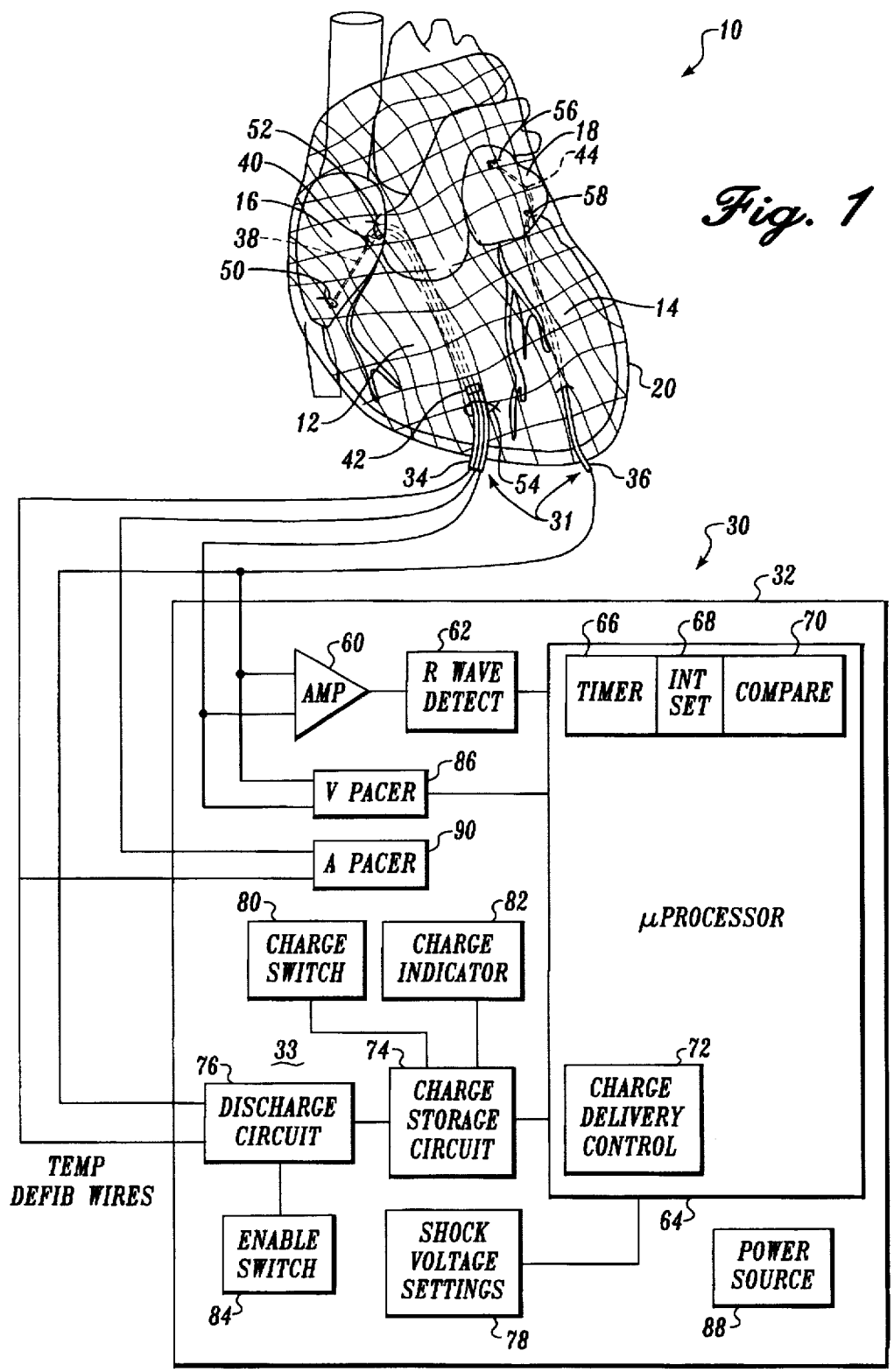
FIG. 1 is a schematic block diagram of a cardioverting and pacing system embodying the present invention.

Referring now to FIG. 1, it illustrates a cardioverting/pacing system 30 embodying the present invention shown in association with a human heart 10 which has undergone surgery and which may require cardioversion of the atria, pacing of the atria, and/or pacing of the ventricles during the post-surgery period. The portions of the heart 10 illustrated in FIG. 1 and which will be referred to hereinafter are the right ventricle 12, the left ventricle 14, the right atrium 16, and the left atrium 18. The heart 10, as illustrated is within the pericardial sac 20 which separates the heart from the lungs (not shown).

The cardioverting system 30 generally includes an external cardiovertor/pacer 32 including a cardiovertor 33, a ventricular pacer 86, and an atrial pacer 90 for providing cardioverting and pacing electrical energy. The system 30 further includes a lead system 31 including a first lead 34 and a second lead 36.

Figure 2:
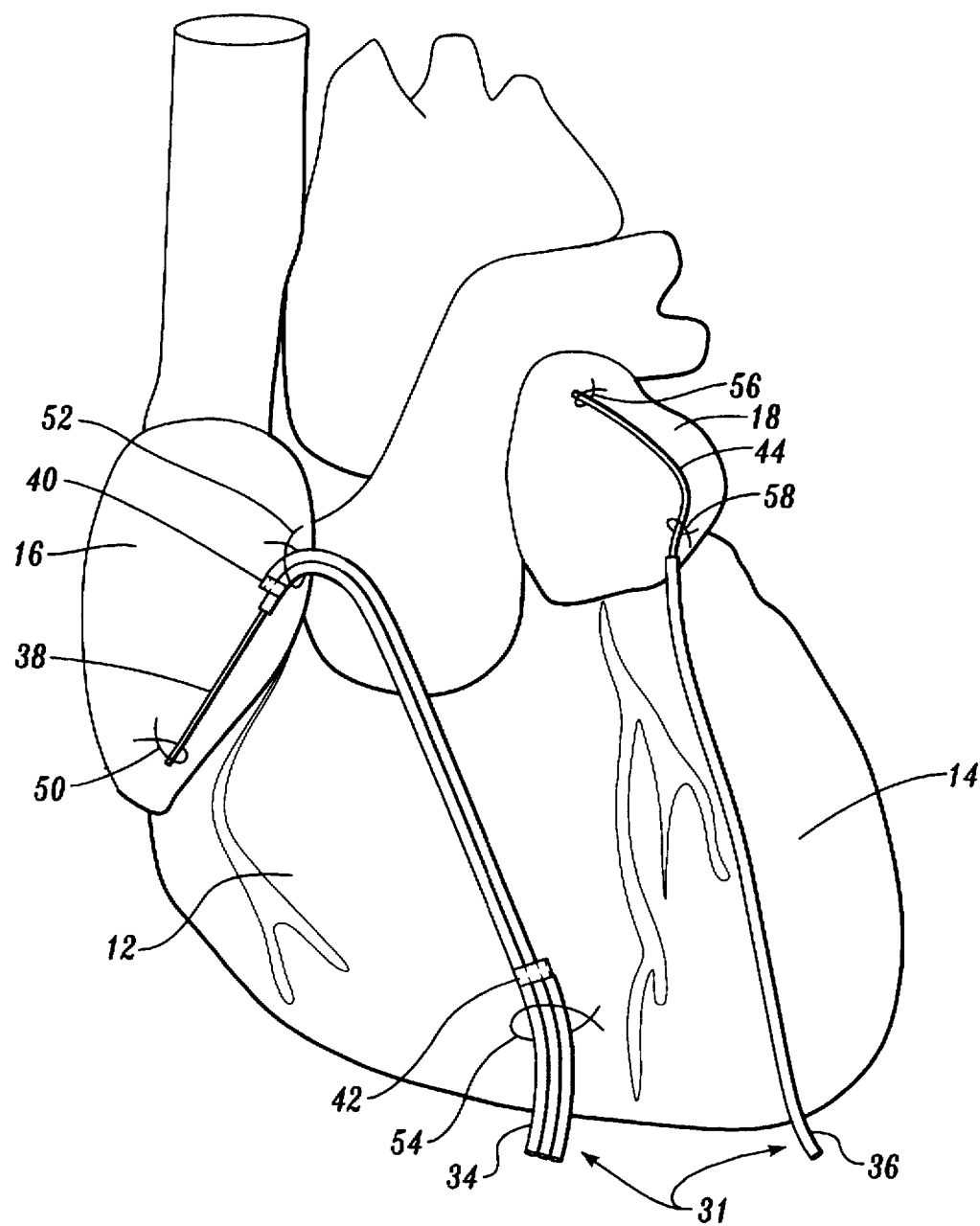
FIG. 2 is a side view, to an enlarged scale, of a human heart illustrating a first temporary cardioverting and pacing lead system embodying the present invention.

As may be best seen in FIG. 2, the first lead 34 is preferably a ribbon cable and includes an atrial cardioverting electrode 38 and an atrial pacing electrode 40. As used herein, the term "cardioverting electrode" is meant to denote an electrode particularly suited for applying cardioverting or defibrillating electrical energy to the heart, as for example, an elongated electrode having a length of about 2 to 8 centimeters and preferably about 6 centimeters. The term "pacing electrode" in contrast, is meant to denote an electrode particularly suited for applying pacing electrical energy to the heart to create, with a low energy, short duration pulse, a high current density locally at the electrode for pacing the heart. Such an electrode is particularly unsuited for cardioversion and may have a length dimension of between 0.2 to 1.25 centimeters, and preferably 1.0 centimeter. The electrodes 38 and 40 are releasably anchored to the atria 16 of the heart 10 by sutures 50 and 52 which have been given a loose suture knot to permit the electrodes 38 and 40 to make electrical contact with the right atrium 16 while permitting the lead 34 and electrodes 38 and 40 to be withdrawn from the patient, as by pulling, to disengage the loose sutures after the patient has recovered sufficiently so as to no longer require arrhythmia monitoring.

Proximal to electrode 40 the lead 34 also includes a ventricular pacing electrode 42 releasably anchored to the right ventricle 12 by another suture 54 in a similar manner with a loose suture knot. The electrode 42 is disposed by the suture 54 in electrical contact with the right ventricle. The electrodes 40 and 42 are preferably formed by a ring which extends around the lead and which is in electrical contact with its corresponding ribbon cable conductor and not in electrical contact with any other ribbon cable conductors. Hence, the electrodes 38–40, and 42 are electrically isolated from each other and spaced apart so that when the atrial cardioverting electrode 38 and the atrial pacing electrode 40 are in electrical contact with one of the atria, such as right atrium 16, the ventricular pacing electrode 42 may be placed in electrical contact with a corresponding ventricle, such as the right ventricle 12.

The second lead 36 similarly includes a cardioverting electrode 44. The electrode 44 is releasably anchored to the left atrium 18 of the heart 10 by suture 56 to extend the electrode 44 along and in electrical contact with the left atrium 18. The proximal end of electrode 44 may also be releasably anchored to the left atrium 18 by suture 58 in a similar manner.

The leads 34 and 36 are preferably placed in the following manner. First, the leads 34 and 38 are inserted through the incision of the pericardium 20 previously made to gain access to the heart. The electrode 38 is then extended along the outer surface of the right atrium 16 for substantially its entire length. The distal end of electrode 38 is then releasably anchored to the right atrium with the loose suture 50. The lead 34 is then releasably sutured to the right atrium at a point just proximal to the electrode 40 with suture 52. Similarly, suture 54 is employed just proximal to electrode 42 to form another releasable anchor. The lead 36 is similarly releasably anchored with sutures 56 and 58 to the left atrium with electrode 44 extending along the left atrium. The patient's chest may then be closed and the lead connected to an external cardiovertor and pacer as described hereinafter. The proximal ends of leads 34 and 36 may be provided with a needle-shaped proximal end. The needle shape permits the proximal end to pierce body tissue for bringing the proximal end of the temporary leads 34 and 36 outside of the chest. Further, it is preferred that the electrodes 38 and 44 be flexible to permit the electrodes to conform to the shape or contour of the atria of the heart to assure continuous electrical contact between the electrodes and the heart. In addition, it is preferred that the impedance of the lead conductors contacting pacing electrodes 40 and 42 be fifteen ohms or less whereas the impedance of the conductors contacting and forming electrodes 38 and 40 be on the order of one ohm. Such a low impedance may be achieved by forming the conductors for electrodes 38 and 44 with stranded wire of stainless steel and providing the conductor with a continuous central core of silver. The conductor may then be provided with insulation up to the electrodes.

Referring again to FIG. 1, the cardiovertor/pacer 33 includes a sense amplifier 60 and an R wave detector 62. The inputs of the sense amplifier 60 are coupled to electrodes 42 and 44 for sensing ventricular activity. The output of the sense amplifier 60 is coupled to the R wave detector 62. The sense amplifier 60, the R wave detector 62, and electrodes 42 and 44 provides detection of ventricular activations or R waves of the heart. The detection of the R waves permits the cardioverting electrical energy applied to the atria to be synchronized to an R wave. Such synchronization is well known in the art. The synchronization may also be accomplished by sensing R waves from a surface ECG.

The cardiovertor 33 further includes a microprocessor 64. The implementation of the microprocessor 64 in accordance with this embodiment of the present invention results in a plurality of functional stages. The stages include a timer 66, an interval set stage 68, a comparator stage 70, and a charge delivery and energy control stage 72.

The microprocessor 64 is arranged to operate in conjunction with a memory (not shown) which may be coupled to the microprocessor by a multiple-bit address bus (not shown) and a bi-directional multiple-bit database (not shown). This permits the microprocessor 62 to address desired memory locations within the memory for executing write or read operations. During a write operation, the microprocessor stores data, such as time intervals or operating parameters in the memory at the addresses defined by multiple-bit addresses conveyed over the address bus and conveys the data to the memory over the multiple-bit data bus. During a read operation, the microprocessor 64 obtains data from the memory at the storage locations identified by the multiple-bit addresses provided over the address bus and receives the data from the memory over the bi-directional data bus.

The cardiovertor 33 further includes a charger and storage capacitor circuit 74 of the type well known in the art which charges a storage capacitor to a peak voltage level determined by a voltage setting control 78 and a discharge circuit 76 for discharging the storage capacitor within circuit 74 for a predetermined time period to provide a controlled discharge output of electrical energy when enabled by an enable switch 84. To that end, the discharge circuit 76 is coupled to the first electrode 38 of the first lead 34 and the second electrode 44 of the second lead 36 for applying the cardioverting electrical energy to the atria.

Associated with the charger and delivery control 72 is a manually operated charge switch 80, a manually operated enable switch 84, and a charge indicator 82. When it is desired to charge the capacitor of circuit 74, the switch 80 is actuated. When the capacitor is charged to a desired peak voltage selected with setting control 78, an indicator, such as an LED, will provide a suitable indication. When the capacitor is fully charged, the enable switch 84 is then activated to initiate discharge of the capacitor or described subsequently.

The ventricular pacemaker circuit 86 may be of the type well known in the art for providing pacing electrical energy pulses. The pacemaker circuit is preferably operable in a demand mode (VVI) and is coupled to the electrodes 42 and 44 of leads 34 and 36 for sensing ventricular activity and providing demand pacing of the heart. Because the electrode 42 is of short length (small surface area) and particularly suited for pacing as compared to the electrode 44 which is comparatively long (large surface area), the pacing pulses will create a maximum current density around electrode 42 for locally stimulating the ventricular myocardium and thus causing the ventricles to be paced.

The atrial pacemaker circuit 90 is also of the type well known in the art for pacing the atria. The atrial pacer is coupled to electrodes 38 and 40 to provide atrial sensing and pacing. The applied atrial pacing pulses cause a sufficient current density around electrode 40 to effectively pace the atria.

Lastly, the cardiovertor/pacer 32 includes a power source 88 for providing power to the electrical components of the atrial cardiovertor 32. The power source 88 may be an AC power supply since the cardiovertor 32 is intended for external use, or it may be a battery if portability of the cardiovertor 32 is preferred.

After the heart surgery is completed, the electrodes 38, 40, and 42 of lead 34 and electrode 44 of lead 34 are attached to the heart as previously described, and the patient's chest is closed, the cardiovertor 32 is coupled to the leads 34 and 36 as illustrated. The pacers 86 and 90 and the cardiovertor 33 will then be ready to pace the ventricles with electrodes 42 and 44, pace the atria with electrodes 40 and 38, or cardiovert the atria with electrodes 38 and 44 as needed. Generally, for pacing either the ventricles or the atria, energy of about 50 microjoules may be sufficient. For cardioverting the atria, cardioverting energies in the range of one to five joules may be sufficient.

If an atrial arrhythmia is detected, a desired peak voltage from which cardioversion is to begin is manually selected with setting control 78. The charger and delivery control switch 80 is then manually actuated. This causes the storage capacitor of circuit 74 to begin being charged. When the voltage on the capacitor reaches the desired peak voltage, the indicator 82 will indicate that the capacitor is fully charged. Next, the enable switch 84 is manually actuated to condition the discharge circuit 76 to initiate the discharge of the storage capacitor within circuit 74 into leads 34 and 36 and electrodes 38 and 44 at the appropriate time to cardiovert the atria. The discharge circuit 76 initiates the discharge of the cardioverting electrical energy under the control of the charger and delivery control 72.

The discharge is preferably synchronized with an R wave. In addition, the timer 66, internal set stage 68, and comparator stage 70 are also preferably utilized as taught in U.S. Pat. No. 5,207,219 to synchronize the appreciation of the cardioverting energy to an R wave which completes a cardiac internal having a duration longer than predetermined minimum interval.

The cardioverting electrical energy is preferably applied for a fixed time period using a time symmetrical biphasic waveform. Because the electrodes 38 and 44 are on the outer surface of the heart, energies between only one and five joules, depending upon the patient, are required for successful cardioversion.

Figure 3:
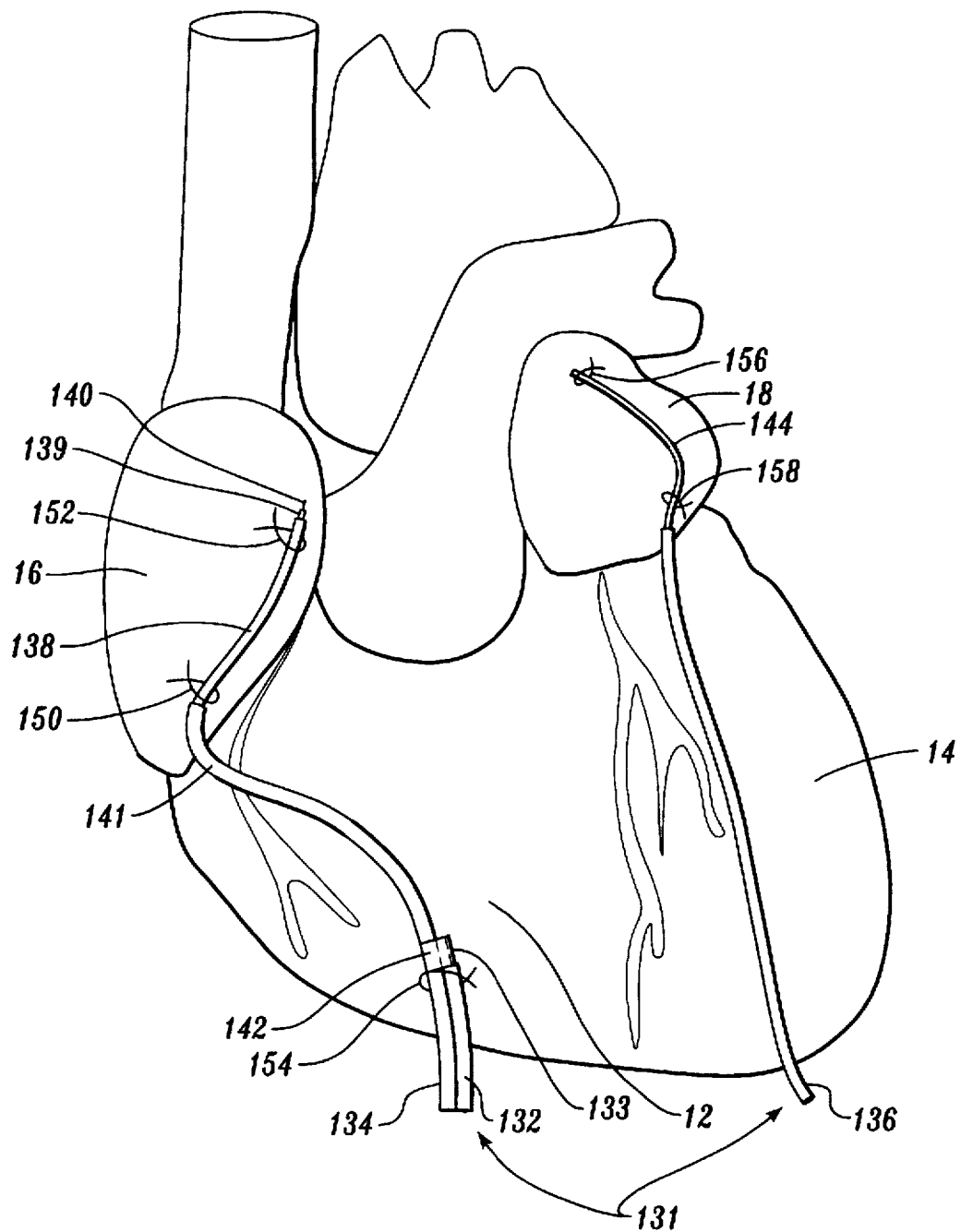
FIG. 3 is a side view, to an enlarged scale, of a human heart illustrating a second temporary cardioverting and pacing lead system embodying the present invention.

Referring now to FIG. 3, it illustrates another lead system 131 embodying the present invention. The lead system 131 includes a first lead 134 and a second lead 136.

The first lead 134 includes an atrial cardioverting electrode 138, an atrial pacing electrode 140, and a ventricular pacing electrode 142. The atrial pacing electrode 140 is at the distal end of lead 134. The atrial cardioverting electrode 138 is proximal to the atrial pacing electrode 140 and the ventricle pacing electrode 142 is proximal to the atria cardioverting electrode 138. The electrodes of lead 134 are also spaced apart such that when electrode 138 is in contact with the atrium 16 as shown, the atrial pacing electrode 140 will be in position to contact the atrium 16 and the ventricular pacing electrode 142 will be in position to contact the corresponding ventricle 12.

The electrodes 138 and 140 are also coaxially disposed with respect to each other. To that end, the electrode 138 is formed by an outer conductor which is separated from the inner conductor forming electrode 140 by an insulating layer 139. An outer insulating layer 141 overlies the outer conductor forming electrode 138. The coaxial lead structure is joined longitudinally with a single conductor insulated wire 132 to form ribbon cable therewith. The wire 132 has a center conductor 133 which contacts the ventricular pacing electrode 142 which may be formed as previously described with regard to electrodes 40 and 42 of FIG. 2. The electrodes 138, 140, and 142 are releasably anchored to the heart by loose sutures 150, 152, and 154 in a manner as previously described.

The lead 136 is a single conductor wire wherein the single conductor forms another atrial cardioverting electrode 144.

The electrode 144 is releasbly anchored to the heart by loose sutures 156 and 158.

In use, electrodes 138 and 144 may be used for cardioverting the atria. Electrodes 138 and 140 may be used for pacing the atria, and electrodes 142 and 144 may be used for pacing the ventricles.

Figure 4:
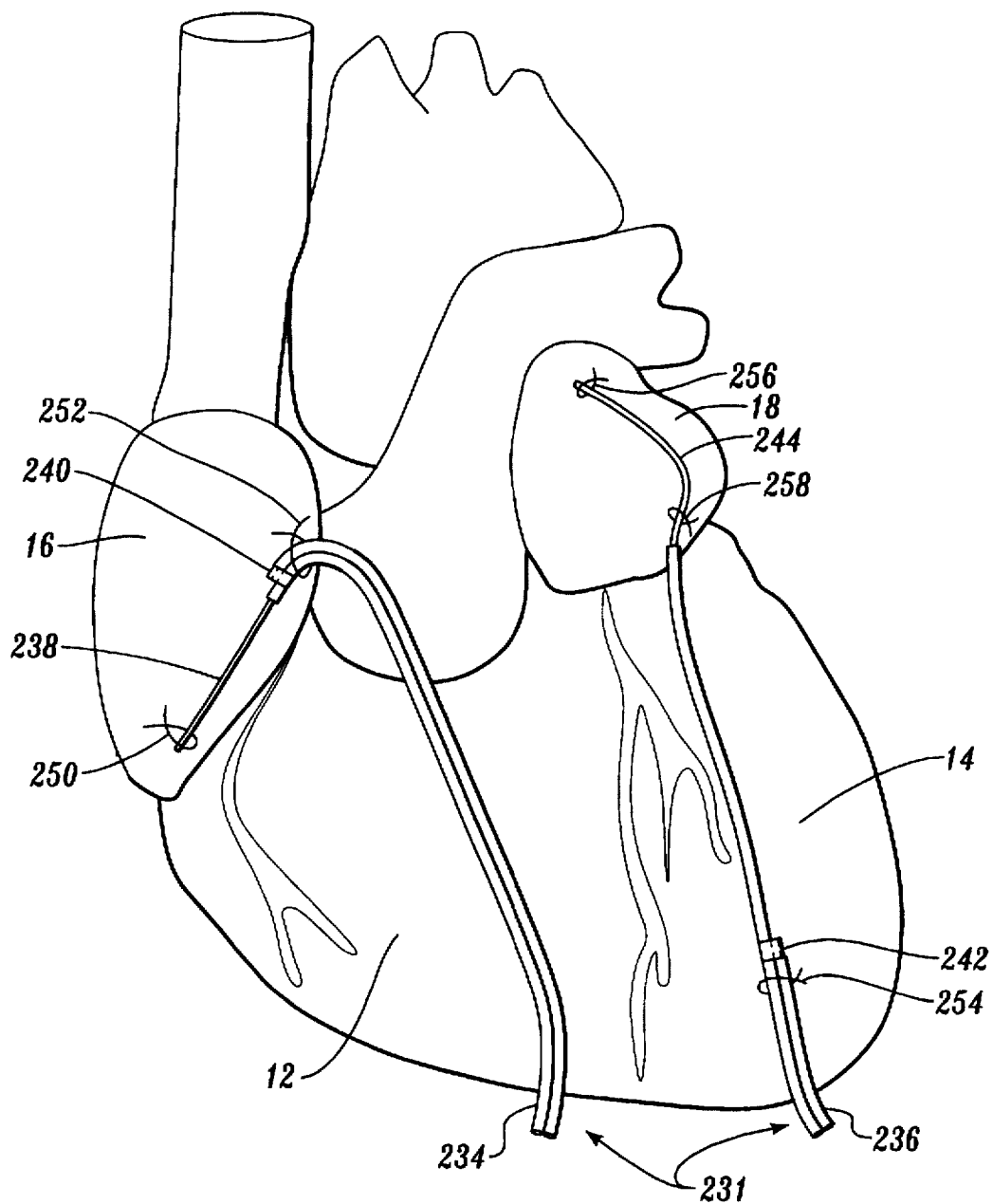
FIG. 4 is a side view, to an enlarged scale, of a human heart illustrating another lead system embodying the present invention.

Referring now to FIG. 4, it illustrates another lead system 231 embodying the present invention. The lead system 231 includes a first lead 234 and a second lead 236. The first lead 234 takes the form of a ribbon cable and includes an atrial cardioverting electrode 238 and an atrial pacing electrode 240. The electrodes 238 and 240 are releasably anchored to the heart by loose sutures 250 and 252 in a manner as previously described. The electrodes of lead 234 are spaced apart such that when electrode 238 is in contact with the atrium 16 as shown, the atrial pacing electrode 240 will also be in position to contact the atrium 16.

The lead 236 also takes the form of a ribbon cable and includes atrial cardioverting electrode 244 and a ventricular pacing electrode 242. The electrodes 244 and 242 are also releasably anchored to the heart by loose sutures 254, 256, and 258.

In use, electrodes 238 and 244 may be used for cardioverting the atria, electrodes 238 and 240 may be used for pacing the atria, and electrodes 242 and 244 may be used for pacing the ventricles. Alternatively, electrodes 238 and 242 may be used for pacing the ventricles.

Figure 5:
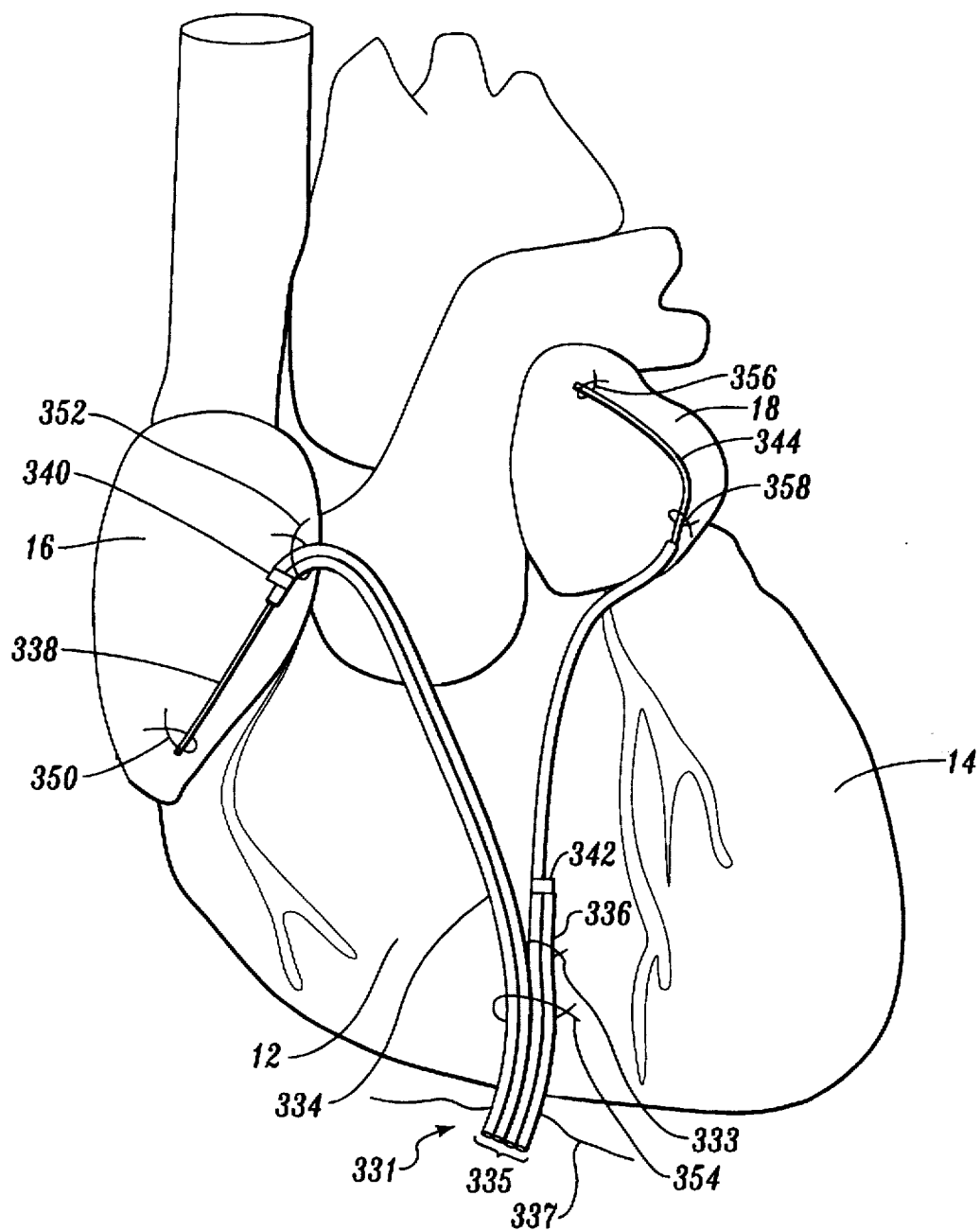
FIG. 5 illustrates a further lead system embodying the present invention wherein first and second leads are joined together to present a single lead body for extraction.

Referring now to FIG. 5, it illustrates another lead system 331 embodying the present invention. The lead system 331 includes a first lead 334 and a second lead 336. The first lead 334 takes the form of a ribbon cable and includes an atrial cardioverting electrode 338 and an atrial pacing electrode 340. The electrodes 338 and 340 are releasbly anchored to the heart by loose sutures 350 and 352 in a manner as previously described. The electrodes of lead 334 are spaced apart such that when electrode 338 is in contact with the atrium 16 as shown, the atrial pacing electrode 340 will also be in position to contact the atrium 16.

The lead 336 also takes the form of a ribbon cable and includes atrial cardioverting electrode 344 and a ventricular pacing electrode 342. The electrodes 244 and 342 are also releasably anchored to the heart by loose sutures 354, 356, and 358.

As will be noted in the figure, the leads 334 and 336 have a longitudinal length and are joined together along their longitudinal lengths from a point of joinder 333. The point of joinder 333 is proximal to the cardioverting electrodes 338 and 344. The point of joinder 333 is also distal to a point of exit 337 from the patient and the joinder continues proximally from the point of joinder 333 past the point of exit 337 from the patient's body. This provides the advantage of having only a single lead body 335 for extraction from the patient when the post-surgery cardioverting and pacing system is no longer needed.

In use, electrodes 338 and 344 may be used for cardioverting the atria, electrodes 338 and 340 may be used for pacing the atria, and electrodes 342 and 344 may be used for pacing the ventricles. Alternatively, electrodes 338 and 342 may be used for pacing the ventricles.

As can thus be seen from the foregoing, the present invention provides an improved post-heart surgery cardioverting systems and post-heart surgery fibrillation and pacing temporary lead system. The leads system of the present invention avoids the need for separate ventricular and atrial pacing heart wires. Hence, the option of ventricular pacing, atrial pacing, and/or atrial cardioversion is made available for post-surgery application with a reduced number of temporary leads. When the patient has sufficiently recovered so as to no longer require pacing or cardioversion, fewer leads need be pulled out of the patient's chest.

While a particular embodiment of the present invention has been shown and described, modifications may be made. For example, the system and method of the present invention may also be utilized to advantage to terminate ventricular tachycardia or even ventricular fibrillation during the post-surgery period. In such an application, the elongated electrodes may be releasably anchored to the ventricles to enable the electrodes to be removed from the patient by pulling on the leads to which the electrodes are attached. Further, the elongated electrodes may be releasably anchored to the pericardium as taught in U.S. Pat. No. 5,403,353. Still further, the system and temporary leads of the present invention may be further employed to provide modes of pacing other than those particularly described herein, such as dual chamber pacing. Further, the system and temporary leads of the present invention may be advantageously used following heart surgery performed with less invasive techniques than open heart surgery. For example, the present invention may find application in connection with heart surgery wherein arthroscopic surgical procedures are employed. Still further, and as previously described, R waves detected from a surface ECG may be used to synchronize the application of the cardioverting energy. Hence, it is therefore intended in the appended claims to cover all such changes and modifications which fall within the true spirit and scope of the invention.

What is claimed is:

1. A post-surgical temporary lead kit for applying atrial cardioverting electrical energy and/or pacing energy to the heart of a post-surgical heart patient when connected between a source of cardioverting and/or pacing energy and a patient's heart, said kit comprising the combination of:

a first lead and a second lead having distal ends adapted to be used beneath the skin and together including at the distal ends a pair of atrial cardioverting electrodes adapted to receive cardioverting energy from the source of cardioverting energy, an atrial pacing electrode adapted to receive pacing electrical energy from the source of pacing energy, and a ventricular pacing electrode adapted to receive pacing electrical energy from the source of pacing energy, the electrodes being electrically isolated from each other before being coupled to the patient's heart; and anchor means adapted to releasably electrically contact each respective atrial cardioverting electrode with a respective given one of the atria, adapted to releasably electrically contact the atrial pacing electrode with one of the atria, and adapted to releasably electrically contact the ventricular pacing electrode with a ventricle, said anchor means being adapted to provide the releasable contact of the electrodes beneath the skin external to the interior of the heart to permit the first lead and the second lead to be pulled from beneath the skin.

2. A lead kit as defined claim 1 wherein the first and second leads each have a longitudinal dimension and are joined together along the longitudinal dimensions beginning from a point proximal to the cardioverting electrodes and distal to and continuing proximally through and past a point of exit from the patient to provide a single lead body for extraction.

3. A post-surgical temporary lead kit for applying atrial cardioverting electrical energy and/or pacing energy to the heart of a post-surgical heart patient when connected between a pulse generator and patient's heart, said kit comprising:

a first lead having an atrial pacing electrode adapted to be connected to the pulse generator, an atrial cardioverting electrode adapted to be coupled to the pulse generator, and a ventricular pacing electrode adapted to be coupled to the pulse generator, the electrodes being electrically isolated from each other before being coupled to the patient's heart and spaced apart so that when the atrial pacing and cardioverting electrodes are in electrical contact with an atrium, the ventricular pacing electrode is adapted to be in electrical contact with a ventricle;

a second lead having an atrial cardioverting electrode adapted to be coupled to the pulse generator; and anchor means adapted to releasably electrically contact the atrial pacing electrode of the first lead with a given one of the atria, adapted to releasably electrically contact the atrial cardioverting electrode of the first lead with the given one of the atria, adapted to releasably electrically contact the ventricular electrode of the first lead with a given one of the ventricles and adapted to releasably electrically contact the atrial cardioverting electrode of the second lead with the other one of the atria, the anchor means being adapted to provide the releasable contact of the electrodes beneath the skin external to the interior of the heart to permit the leads to be pulled from beneath the skin.

4. A lead kit as defined in claim 3 wherein the first lead includes a distal end and a proximal end, wherein the atrial pacing electrode of the first lead is at the distal end of the first lead, wherein the atrial cardioverting electrode of the first lead is proximal to the atrial pacing electrode of the first lead, and wherein the ventricular pacing electrode of the first lead is proximal to the atrial cardioverting electrode of the first lead.

5. A lead kit as defined in claim 4 wherein the atrial pacing electrode of the first lead is coaxially disposed in relation to the atrial cardioverting electrode of the first lead.

6. A lead kit as defined in claim 3 wherein the first lead includes a distal end and a proximal end, wherein the atrial cardioverting electrode of the first lead is at the distal end of the first lead, wherein the atrial pacing electrode of the first lead is proximal to the atrial cardioverting electrode of the first lead, and wherein the ventricular pacing electrode of the first lead is proximal to the atrial pacing electrode of the first lead.

7. A lead kit as defined in claim 6 wherein the first lead is a ribbon cable.

8. A post-surgical temporary lead kit for applying atrial cardioverting electrical energy and/or pacing energy to the heart of a post-surgical heart patient when connected between a pulse generator and a patient's heart, said lead kit comprising the combination of:

a first lead having a proximal end and a distal end, the distal end having an atrial pacing electrode adapted to be coupled to the pulse generator for receiving pacing electrical energy and an atrial cardioverting electrode adapted to be coupled to the pulse generator for receiving cardioverting electrical energy, the electrodes of the first lead being electrically isolated from each other and spaced apart so that when the cardioverting electrode of the first lead is in electrical contact with an atrium, the atrial pacing electrode of the first lead is adapted for electrical contact with the atrium;

a second lead having a proximal end and a distal end, the distal end having an atrial cardioverting electrode adapted to be coupled to the pulse generator for receiving cardioverting electrical energy and a ventricular pacing electrode adapted to be coupled to the pulse generator for receiving pacing electrical energy, the electrodes of the second lead being electrically isolated from each other and spaced apart so that when the atrial cardioverting electrode of the second lead is in electrical contact with an atrium, the ventricular electrode of the second lead is adapted for electrical contact with a corresponding ventricle, the distal ends of the leads including the electrodes being adapted to be beneath the skin and the proximal ends of the leads being adapted to be outside the skin for connection to the pulse generator; and anchor means adapted to releasably electrically contact the atrial cardioverting electrode of the first lead with a given one of the atria, adapted to releasably electrically contact the atrial pacing electrode of the first lead with the given one of the atria, adapted to releasably electrically contact the atrial cardioverting electrode of the second lead with the other one of the atria and adapted to releasably electrically contact the ventricular pacing electrode of the second lead with a ventricle corresponding to the other one of the atria, the anchor means being adapted to provide the releasable contact of the electrodes beneath the skin external to the interior of the heart to permit the leads to be pulled entirely from beneath the skin upon the pulling of the proximal ends of the leads.

9. A lead kit as defined in claim 8 wherein the atrial pacing electrode of the first lead is proximal to the atrial cardioverting electrode of the first lead.

10. A lead kit as defined in claim 9 wherein the first lead is a ribbon cable.

11. A lead kit as defined in claim 8 wherein the atrial cardioverting electrode of the second lead is distal to the ventricular pacing electrode.

12. A lead kit as defined in claim 11 wherein the second lead is a ribbon cable.

13. A lead kit as defined in claim 8 wherein the first and second leads each have a longitudinal dimension and are joined together along the longitudinal dimensions beginning from a point proximal to the cardioverting electrodes and distal to and continuing proximally through and past a point to exit from the patient to provide a single lead body for extraction.

* * * * *